(12) United States Patent
Fujisawa

(10) Patent No.: US 8,126,227 B2
(45) Date of Patent: Feb. 28, 2012

(54) X-RAY COMPUTED TOMOGRAPHIC APPARATUS AND MEDICAL IMAGE PROCESSING APPARATUS

(75) Inventor: Yasuko Fujisawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1029 days.

(21) Appl. No.: 11/950,115

(22) Filed: Dec. 4, 2007

(65) Prior Publication Data

US 2008/0130824 A1 Jun. 5, 2008

(30) Foreign Application Priority Data

Dec. 4, 2006 (JP) ................. 2006-327205

(51) Int. Cl.
*G06K 9/00* (2006.01)

(52) U.S. Cl. .............. 382/128; 128/922; 378/4

(58) Field of Classification Search .......... 382/100, 382/128, 129, 130, 131, 132; 128/922; 378/4–27
See application file for complete search history.

(56) References Cited

U.S. PATENT DOCUMENTS

| 5,396,418 | A  | * | 3/1995 | Heuscher ................... 378/15 |
| 5,647,360 | A  | * | 7/1997 | Bani-Hashemi et al. ..... 600/425 |
| 6,373,920 | B1 | * | 4/2002 | Hsieh ..................... 378/98.11 |
| 6,442,235 | B2 | * | 8/2002 | Koppe et al. ................ 378/62 |
| 6,711,433 | B1 | * | 3/2004 | Geiger et al. ............. 600/431 |

FOREIGN PATENT DOCUMENTS

JP 8-79628 3/1996

* cited by examiner

*Primary Examiner* — Anand Bhatnagar
(74) *Attorney, Agent, or Firm* — Oblon, Spivak, McClelland, Maier & Neustadt, L.L.P.

(57) ABSTRACT

An X-ray computed tomographic apparatus includes an X-ray tube which generates X-rays, an X-ray detector which detects X-rays transmitted through a subject and generates projection data, and a reconstruction unit which generates a plurality of original volume data at different scanning times based on the projection data. This apparatus includes an unit which obtains difference volume data corresponding different scanning times by performing difference processing between original volume data at adjacent scanning times, an unit which extracts a blood vessel image on the basis of original volume data before and after the injection of a contrast medium, and an unit which generates a display image by providing the blood vessel image with color or luminance information corresponding to the arrival time of the contrast medium on the basis of the blood vessel image and the plurality of difference volume data corresponding to the different scanning times.

20 Claims, 16 Drawing Sheets

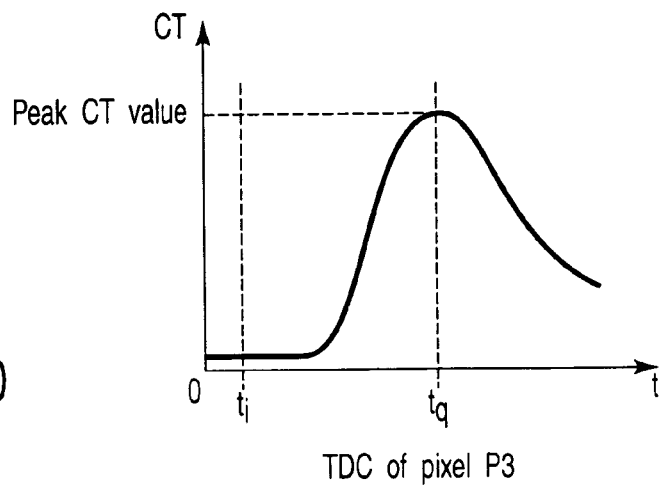
FIG. 10  TDC of pixel P3
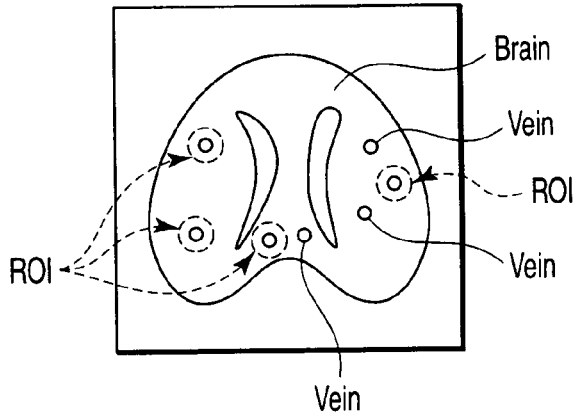
FIG. 11
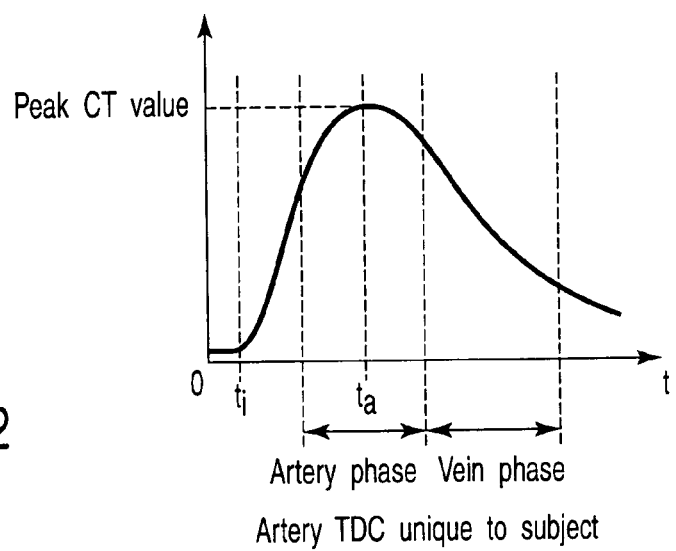
FIG. 12  Artery TDC unique to subject Artery phase volume data file (VA)

Artery running volume data file (VB)

FIG. 16
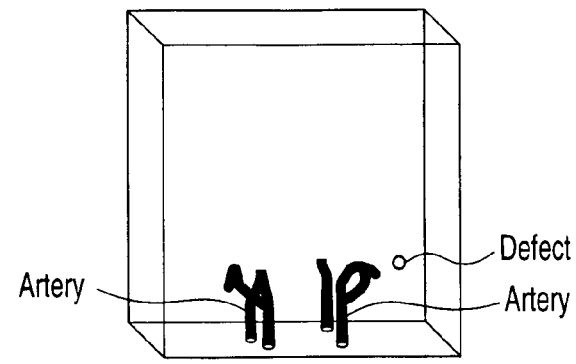
(a) Difrrerence volume data file (VC1)
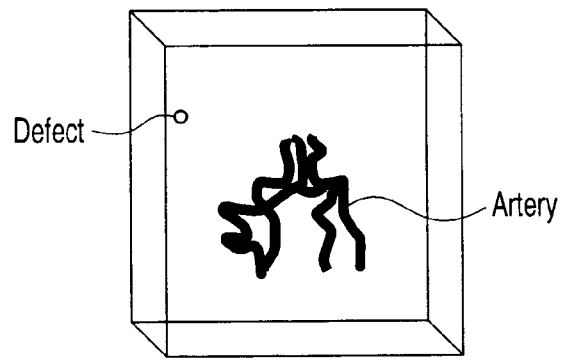
(b) Difrrerence volume data file (VCa)
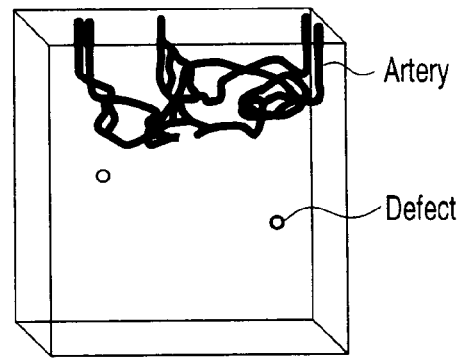
(c) Difrrerence volume data file (VCb)

- Blood vessel portion of (VCb)
- Blood vessel portion of (VCa)
- Blood vessel portion of (VC1)

Defect

Artery volume data (VD)

Display image provided with color information

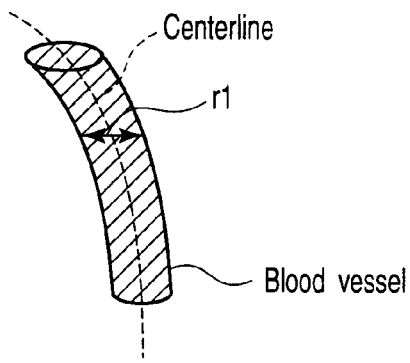
F I G. 2 1
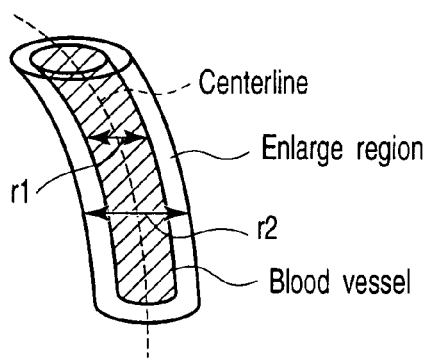
F I G. 2 2
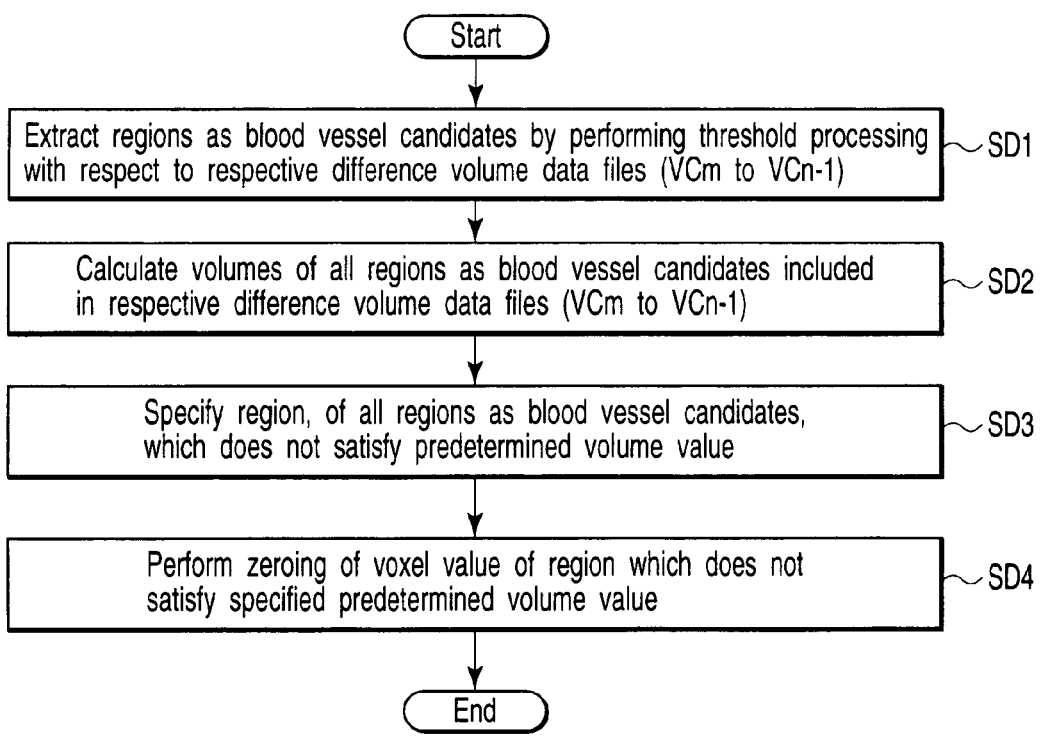
F I G. 2 3

X-RAY COMPUTED TOMOGRAPHIC APPARATUS AND MEDICAL IMAGE PROCESSING APPARATUS

CROSS-REFERENCE TO RELATED APPLICATIONS

This application is based upon and claims the benefit of priority from prior Japanese Patent Application No. 2006-327205, filed Dec. 4, 2006, the entire contents of which are incorporated herein by reference.

BACKGROUND OF THE INVENTION

1. Field of the Invention

The present invention relates to an X-ray computed tomographic apparatus and a medical image processing apparatus which generate a plurality of volume data files at different scanning times with respect to the same scanning region of a subject to be examined.

2. Description of the Related Art

An X-ray computed tomographic apparatus (multi-slice CT) using a multi-slice type or two-dimensional detector executes contrast medium examination. In contrast medium examination in this multi-slice CT, repeatedly radiographing the same scanning region of a subject to be examined after the injection of a contrast medium makes it possible to obtain chronological volume data representing the distribution state of the contrast medium in volume data at each scanning time. Observing a three-dimensional image based on this chronological volume data allows to grasp a blood vessel running state. However, it is impossible to grasp a blood flow state by using this three-dimensional image.

BRIEF SUMMARY OF THE INVENTION

The present invention has been made in consideration of the above situation, and has as its object to provide an X-ray computed tomographic apparatus and a medical image processing apparatus which allow to grasp a blood flow state in multi-slice CT.

According to an aspect of the present invention, it is provided that an X-ray computed tomographic apparatus which comprises: an X-ray tube which generates X-rays; an X-ray detector which detects X-rays transmitted through a subject to be examined and generates projection data; a reconstruction unit which generates a plurality of original volume data at different scanning times on the basis of the projection data; a position-matching unit which performs position-matching between said plurality of original volume data; a difference volume data generating unit which obtains a plurality of difference volume data by performing difference processing between the original volume data at the different scanning times by using said plurality of original volume data after the position-matching; and a display image generating unit which generates a display image provided with color or luminance information corresponding to at least one of an arrival time of a contrast medium, a difference volume, a temporal change amount of difference volume, and blood flow velocity information on the basis of the plurality of difference volume data.

According to another aspect of the present invention, it is provided that a medical image processing apparatus which acquires volume data having three-dimensional information in a subject to be examined, the apparatus which comprises: an X-ray tube which generates X-rays; a storage unit which stores a plurality of original volume data at different scanning times which are acquired by injecting a contrast medium into the subject; a position-matching unit which performs position-matching between said plurality of original volume data; a difference volume data generating unit which obtains a plurality of difference volume data by performing difference processing between the original volume data at the different scanning times by using said plurality of original volume data after the positioning; and a display image generating unit which generates a display image provided with color or luminance information corresponding to at least one of an arrival time of a contrast medium, a difference volume, a temporal change amount of difference volume, and blood flow velocity information on the basis of the plurality of difference volume data.

BRIEF DESCRIPTION OF THE SEVERAL VIEWS OF THE DRAWING

FIG. 10 is a graph showing a contrast medium time density curve (TDC) at a pixel P3 of the central slice image in FIG. 7;

FIG. 11 is a view showing how a region of interest (ROI) is set with respect to a mid-plane image associated with step SA3 in FIG. 5;

FIG. 12 is a graph showing a contrast medium time density curve (TDC) in the region of interest (ROI) in FIG. 11;

FIGS. 16(a) to 16(c) are views showing a plurality of difference volume data files generated in step S03 in FIG. 2;

FIG. 21 is a view for explaining the processing of specifying the position coordinates of the centerline of a blood vessel in step SC1 in FIG. 20;

FIG. 22 is a view for explaining the processing of enlarging a blood vessel region in step SC2 in FIG. 20;

FIG. 23 is a flowchart showing a processing procedure in residue removal routine 2 in FIG. 2;

DETAILED DESCRIPTION OF THE INVENTION

Figure 1:
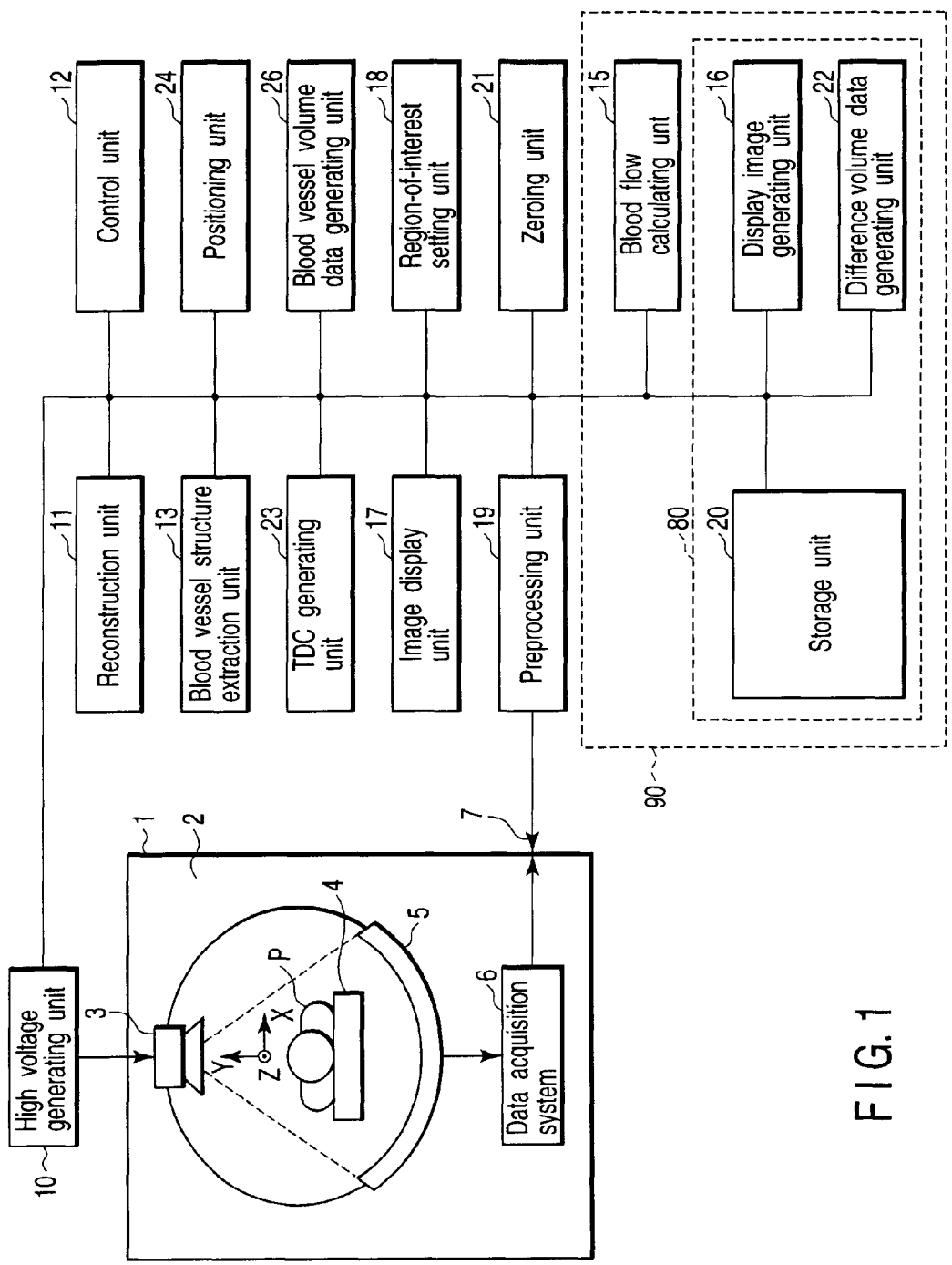
FIG. 1 is a block diagram showing the arrangement of an X-ray computed tomographic apparatus according to an embodiment of the present invention.

The first to fourth embodiments of the present invention will be described below with reference to the views of the accompanying drawing. Note that in the following description, the same reference numerals denote constituent elements having almost the same functions and arrangements, and a repetitive description will be made only when required.

First Embodiment

An embodiment of the present invention will be described with reference to the views of the accompanying drawing.

FIG. 1 shows the arrangement of an X-ray computed tomographic apparatus according to an embodiment of the present invention. Note that X-ray computed tomographic apparatuses include various types of apparatuses, e.g., a rotate/rotate-type apparatus in which an X-ray tube and an X-ray detector rotate together around a subject to be examined, and a stationary/rotate-type apparatus in which many detection elements are arrayed in the form of a ring, and only an X-ray tube rotates around a subject to be examined. The present invention can be applied to either type. This embodiment will exemplify the rotate/rotate type.

The X-ray computed tomographic apparatus includes a gantry 1. The gantry 1 rotatably supports an annular or disk-like rotating frame 2. The rotating frame 2 includes an X-ray tube 3 and an X-ray detector 5 which face each other through a subject P placed on a top 4 in a scanning region. For the sake of descriptive convenience, the rotation axis of the rotating frame 2 is defined as the Z-axis, a scanning central axis connecting the focal point of the X-ray tube 3 and the center of the X-ray detector 5 is defined as the Y-axis, and an axis perpendicular to the Y-Z plane is defined as the X-axis. At the time of scanning, a subject to be examined is placed in the scanning region such that the body axis almost coincides with the Z-axis. This XYZ coordinate system forms a rotational coordinate system having the Z-axis as a rotation center. The X-ray tube 3 receives a high voltage and filament current from a high voltage generating unit 10. If the X-ray detector 5 is a multi-slice type, it has a plurality of detection element arrays which have a plurality of channels in the channel direction (X-axis) and are arranged in the slice direction (Z-axis). If the X-ray detector 5 is of a two-dimensional array type, it has a plurality of X-ray detection elements which are densely distributed in both the channel direction (X-axis) and the slice direction (Z-axis).

A control unit 12 controls the rotation of the rotating frame 2 and sequentially performs CT scanning with respect to the same scanning region of the subject P. More specifically, the rotating frame 2 continuously rotates at a constant angular velocity, and the X-ray tube 3 generates X-rays continuously or for each constant angle.

A data acquisition system (DAS) 6 is connected to the X-ray detector 5. The data acquisition system 6 converts a current signal output from the X-ray detector 5 for each channel into a voltage, amplifies it, and further converts it into a digital signal. The data (pure raw data) acquired by the data acquisition system 6 is sent to a preprocessing unit 19 through a noncontact type or slip-ring type data transmission unit 7 using light or magnetism. The preprocessing unit 19 performs preprocessing for pure raw data, e.g., correction for sensitivity nonuniformity between channels and correction for an extreme decrease in signal intensity or signal omission due to an X-ray absorber, mainly a metal portion, and the like.

A reconstruction unit 11 generates a plurality of volume data files (time-series volume data files) at different scanning times on the basis of the data (projection data or raw data) corrected by the preprocessing unit 19. A plurality of volume data files at different scanning times generated by the reconstruction unit 11 will be referred to as original volume data files VO.

A position-matching unit 24 registers (position-matching) a plurality of original volume data files to original volume data files at the reference time (before the injection of a contrast medium). This positioning is performed to correct the positional shifts of a bone, internal organ, and blood vessel of each original volume data file due to respiration, body movement, and the like.

A difference volume data generating unit 22 takes differences between original volume data files at adjacent scanning times after the injection of the contrast medium to generate a plurality of difference volume data files VC. That is, in each difference volume data file, there is left a region into which a contrast medium has flown while riding on the flow of blood (blood flow) at the intervals between adjacent scanning times (to be referred to as scan time intervals hereinafter) or a region from which the contrast medium has flown out. This left region will be referred to as a blood vessel portion. Since the contrast medium travels in a blood vessel while riding on a blood flow, the left region represents the movement amount of the blood flow in a scan interval. The volume of a blood vessel portion is equal to the volume of a blood flow traveling in the blood vessel in the scan time interval.

In order to specify an artery phase and a vein phase, this apparatus comprises a TDC generating unit 23 and a region-of-interest setting unit 18.

The TDC generating unit 23 generates the density change curve (the time-density curve to be referred to as the TDC hereinafter) of the contrast medium with respect to a given pixel or a region of interest (ROI). A TDC is obtained by plotting a temporal change in CT value in a given pixel or ROI (Region Of Interest). The TDC generating unit 23 specifies the maximum CT value (to be referred to as the peak CT value hereinafter) of a TDC, and specifies an artery phase and a vein phase on the basis of the peak CT value. In this case, the artery phase is a period during which the arteries in a scanning region of interest are stained with a contrast medium, and the vein phase is a period during which the veins in the scanning region of interest are stained with the contrast medium. These artery and vein phases are the periods of the original volume data files VO to be combined in combining processing to be described later.

The region-of-interest setting unit 18 identifies the positions of a given TDC at which it has waveforms approximate to a reference artery waveform and a reference vein waveform. The region-of-interest setting unit 18 then sets a region of interest at and near pixels including pixels on the identified artery and vein.

A blood vessel structure extraction unit 13 generates a single artery phase or vein phase volume data file VA by combining (to be referred to as adding and averaging hereinafter) of all the original volume data files in the artery phase or vein phase. The artery phase or vein phase volume data file VA is a volume data file containing arteries or veins and internal tissue without any residue. The residue is occurred by subtraction after position-matching (or registration). Obviously, adding and averaging all the original volume data files VO make it possible to generate the single volume data file VA containing all blood vessels and internal tissues. All blood vessels include not only blood vessels belonging to an artery phase and a vein phase but also blood vessels belonging to neither of them. The blood vessel structure extraction unit 13 then takes a difference between the volume data file VA obtained by adding and averaging in a desired period (an artery phase, a vein phase, or all periods) and an original volume data file VO1 before the injection of a contrast medium, thereby generating a blood vessel running volume data file VB which contains only blood vessels in a desired period without any background (internal tissue and residue) and extracting (specifying) blood vessel running (a blood vessel image representing a blood vessel structure).

A blood vessel volume data generating unit 26 extracts a plurality of blood vessel portions from a plurality of artery or vein difference volume data files, and generates an artery or vein volume data file VD by overlaying these blood vessel portions along blood vessel running. The artery or vein volume data file VD is a volume data file obtained by overlaying many individually distinguishable blood vessel portions along blood vessel running.

A blood flow calculating unit 15 calculates the volume of a blood vessel portion (blood flow change amount) first to obtain blood flow velocity information such as the flow velocity of blood in a blood vessel (to be referred to as a blood flow velocity hereinafter). The blood flow calculating unit 15 then calculates a blood flow velocity on the basis of scan time intervals associated with the blood vessel portion and the volume of the blood vessel portion. The blood flow calculating unit 15 also assigns the blood vessel portion with plus or minus indicating the direction of the blood flow.

A display image generating unit 16 generates a three-dimensional image (display image) by providing color or luminance information for each blood vessel portion of blood vessel running in the blood vessel volume data file VD on the basis of the scanning time (i.e., the time when the contrast medium has reached each blood vessel portion), the volume of each blood vessel portion, the blood flow velocity, and the like, and performing MPR processing (Multi Planar Reconstruction) and rendering processing.

A zeroing unit 21 removes a residue from the difference volume data file VC by zeroing the voxel value of a residue region contained in the difference volume data file VC on the basis of the blood vessel running volume data file VB.

A storage unit 20 stores various data such as various volume data files of the generated original volume data VO, the difference volume data VC, and the like, and display images.

Figure 2:
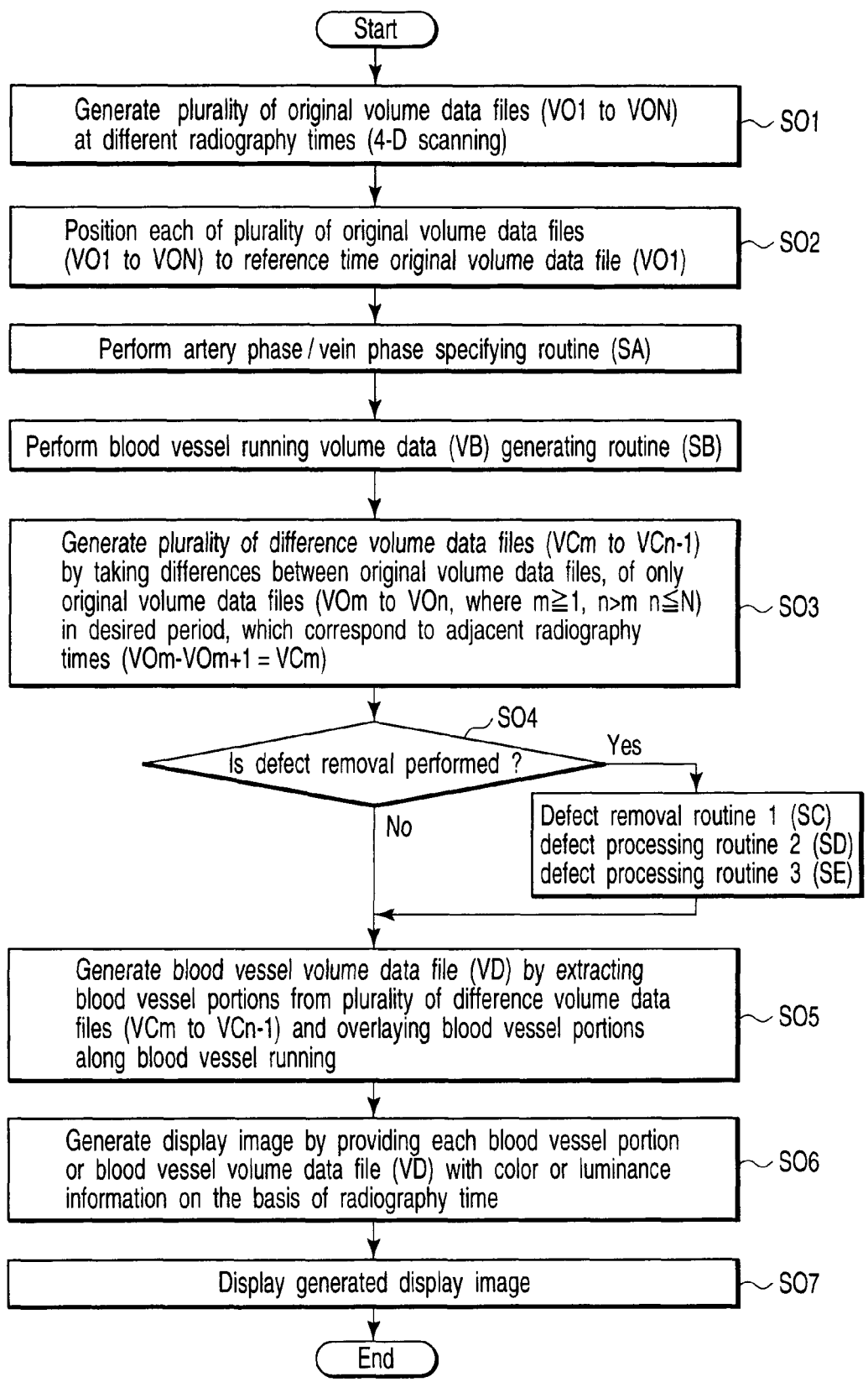
FIG. 2 is a flowchart showing a processing procedure in the first embodiment of the present invention.

A processing procedure in the first embodiment will be described below with reference to FIG. 2.

First of all, CT scanning is performed a plurality of number of times with respect to the same scanning region while a contrast medium is injected, and the reconstruction unit 11 generates a plurality of original volume data files VO1 to VON on the basis of the obtained projection data (step SA1). The original volume data file VO1 is an original volume data file before the contrast medium flows into the scanning region. The original volume data file VO1 will be referred to as the reference time volume data file VO1. As the time elapses from the reference time, volume data files VO1, VO2, . . . , VON are generated. As a result, the reconstruction unit 11 generates a total of N original volume data files.

Figure 3:
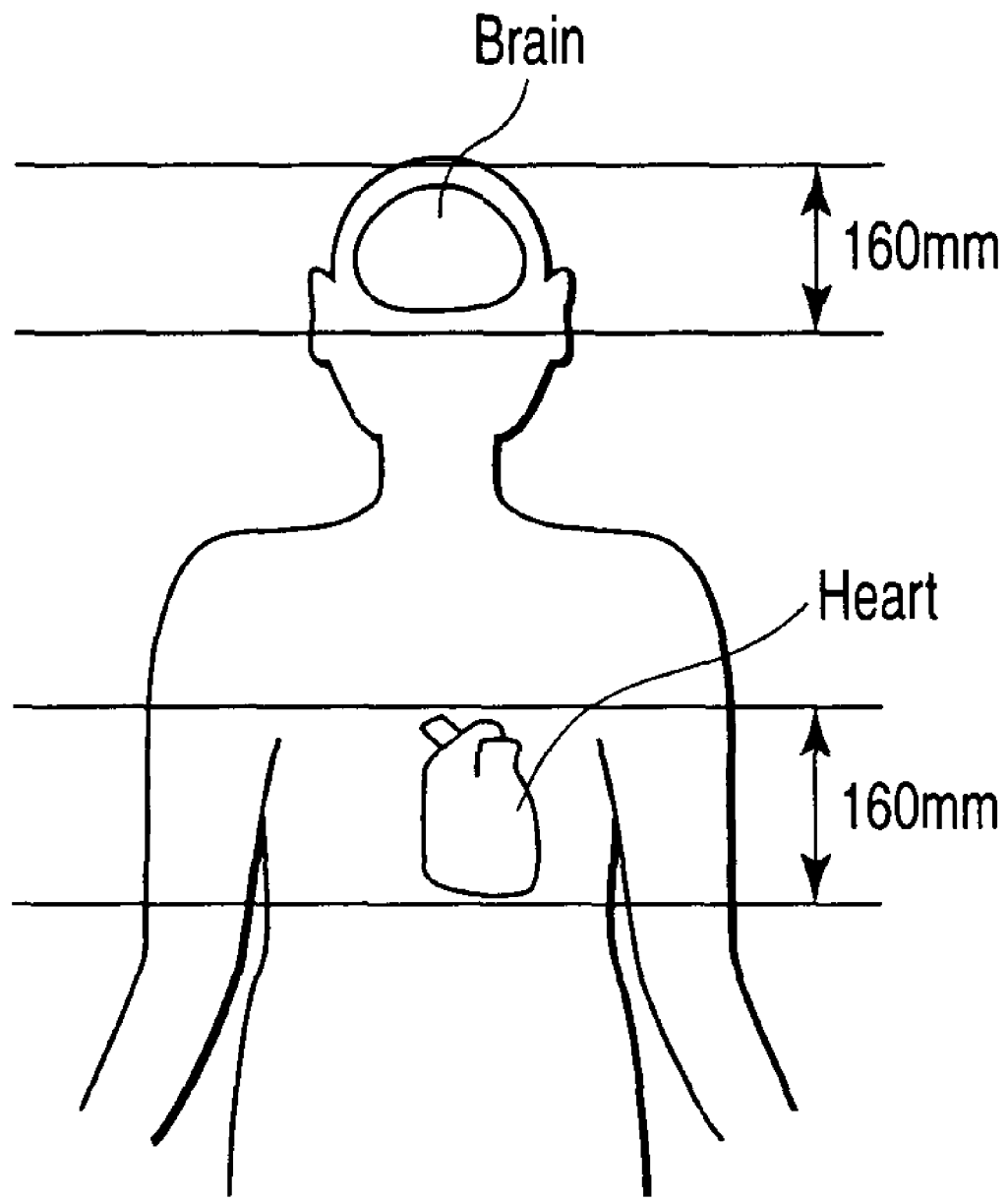
FIG. 3 is a view showing the relationship between the size of the scanning region of an X-ray detector in FIG. 1 and the size of a subject to be examined.

In the first embodiment, the blood vessels represented by volume data files are those in a head portion. Obviously, however, the scanning region is not limited to the head portion, and the present invention can be applied to any region. In the first embodiment, the X-ray detector 5 can acquire projection data of a scanning region having a length of 160 mm in the body axis direction (Z-axis) at once. However, the present invention is not limited to this, and can be applied to a region having a length smaller than 160 mm. FIG. 3 is a view showing the relationship between the size of a scanning region having a length of 160 mm in the body axis direction (Z-axis) and the size of a subject to be examined. As shown in FIG. 3, a scanning region having a length of 160 mm is large enough to include the entire head portion (brain) or the entire chest portion (heart and the like).

Figure 4:
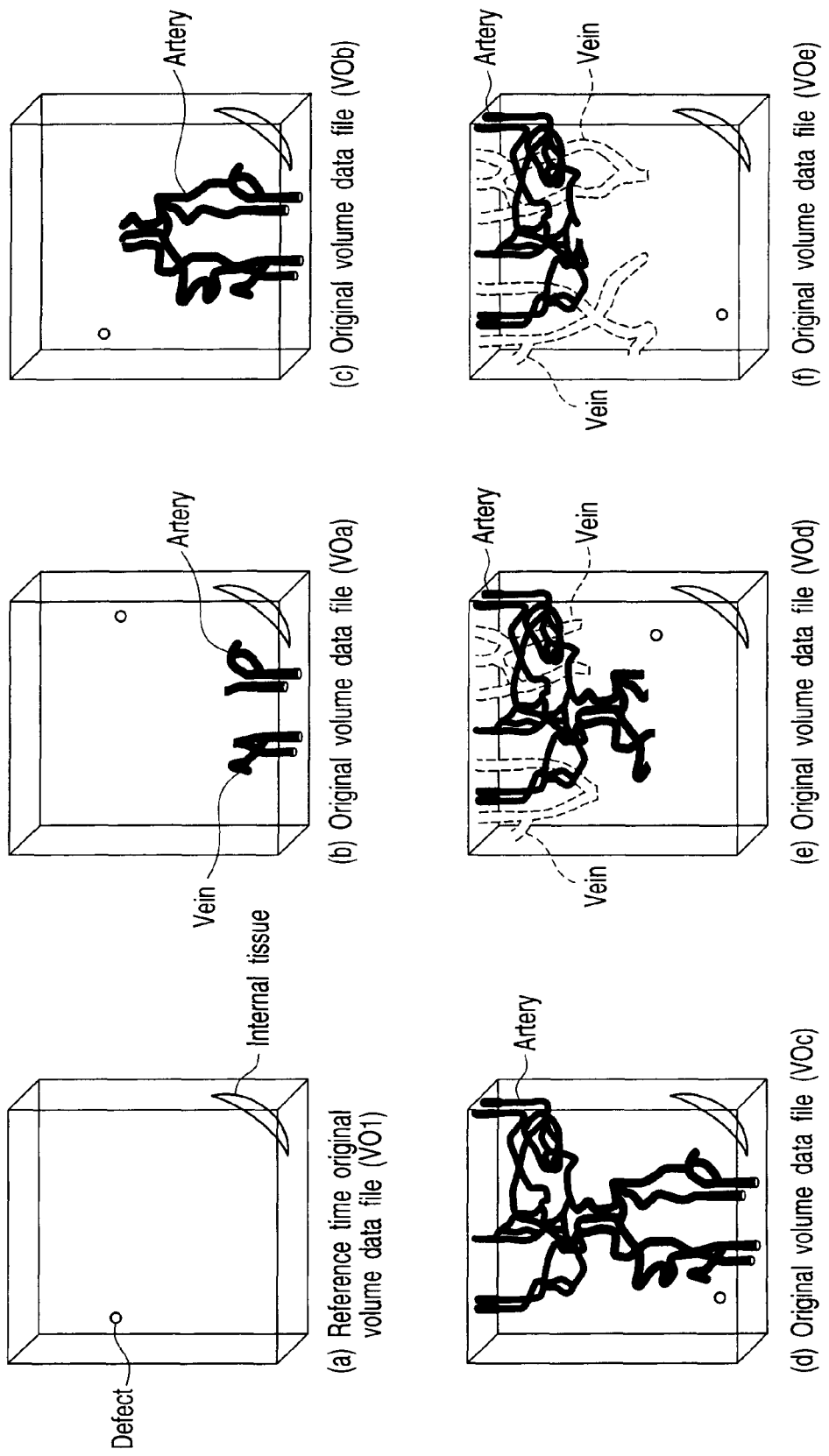
FIG. 4 is view showing a plurality of original volume data files at different scanning times which are generated in step S01 in FIG. 2.

FIGS. 4A to 4F are views showing the original volume data files VO1 to VON obtained in step S01. Assume that in the first embodiment, a contrast medium flows into arteries in the head portion, and then flows into veins. The blood vessels indicated by the solid lines in FIGS. 4B to 4F are arteries, and those indicated by the broken lines are veins. FIG. 4A shows the reference time original volume data file VO1. FIG. 4B shows an original volume data file VOa at the time when the contrast medium begins to flow into arteries. FIG. 4C shows an original volume data file VOb at the time when the contrast medium flows to near the middle portions of the arteries. FIG. 4D shows an original volume data file VOc at the time when the contrast medium flows through the entire arteries. FIG. 4E shows an original volume data file VOe at the time when the contrast medium flows out from the arteries of interest, no contrast medium remains in the lower end portions of the arteries, and the contrast medium begins to flow into the veins. FIG. 4F shows the original volume data file VOe at the time when the contrast medium is left in only the upper end portions of the arteries, and flows to near the middle portions of the veins. The suffixes 1, a, b, c, d, e, and N of VO are related as 1<a<b<c<d<e<N, and represent scanning times. The original volume data files VO1 to VON contain internal tissues (bones and the like) and residues in addition to a contrast medium.

The position-matching unit 24 positions each of the plurality of original volume data files VO1 to VON to the reference time original volume data file VO1 (step S02).

Figure 5:
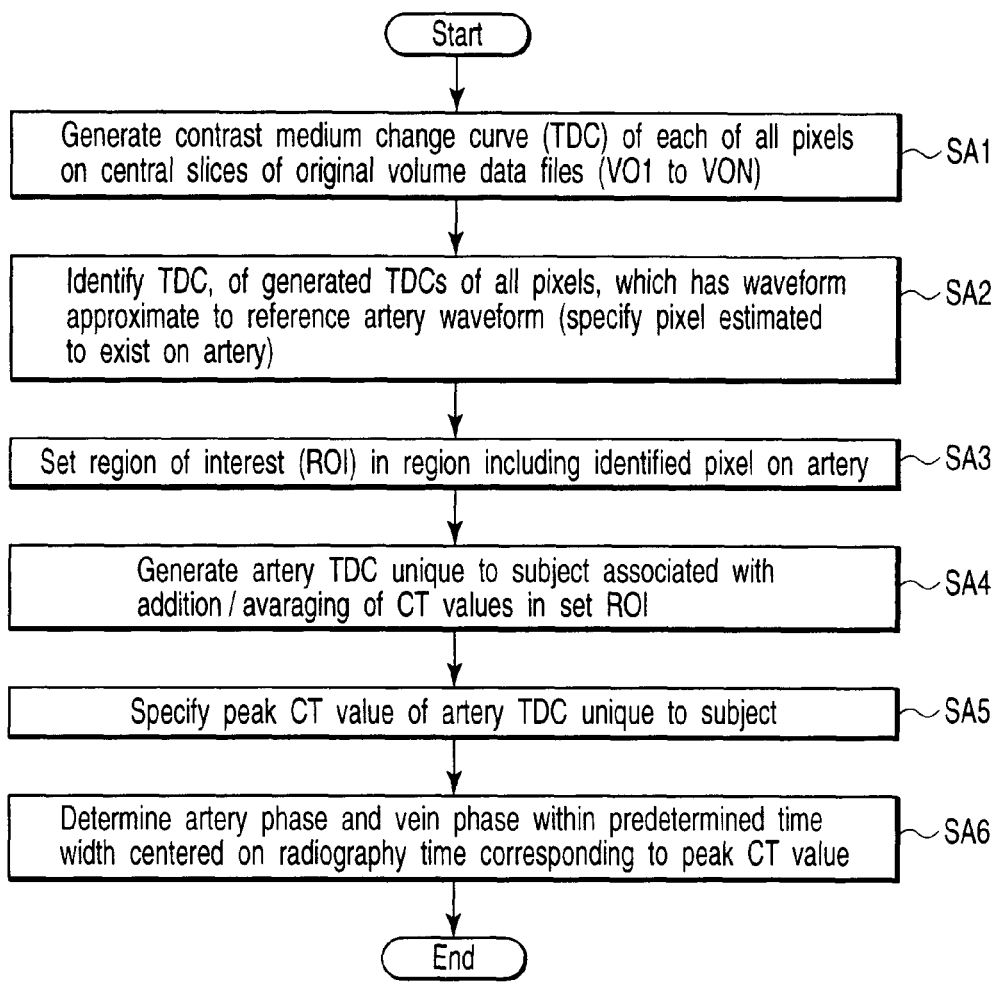
FIG. 5 is a flowchart showing a processing procedure in an artery phase/vein phase specifying routine SA in FIG. 2.

After step S02, an artery phase/vein phase specifying routine SA for specifying an artery phase and a vein phase is started. A processing procedure in the artery phase/vein phase specifying routine SA will be described below with reference to FIG. 5. Consider, for the sake of simplicity, only a case wherein an artery phase is specified in the artery phase/vein phase specifying routine SA.

Figure 6:
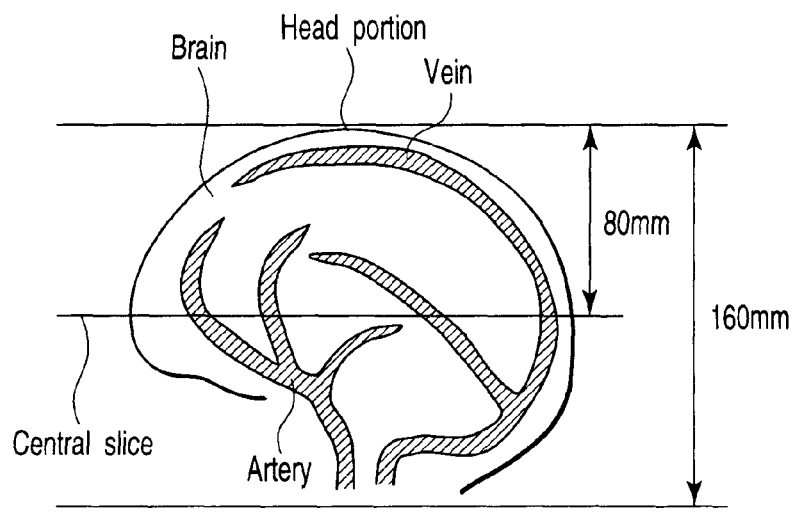
FIG. 6 is a view showing the scanning region of the X-ray detector in FIG. 1, a head portion, and a central slice.

First of all, the TDC generating unit 23 generates a TDC with respect to each pixel on the central slice of each of the original volume data files VO1 to VON (step SA1). FIG. 6 shows the positional relationship between the head portion, the scanning region, and the central slice. As shown in FIG. 6, the scanning region having a length of 160 mm in the body axis direction (Z-axis) includes the entire head portion (brain). In general, the position at 80 mm as the center of 160 mm almost coincides with the center of the head portion (brain).

Figure 7:
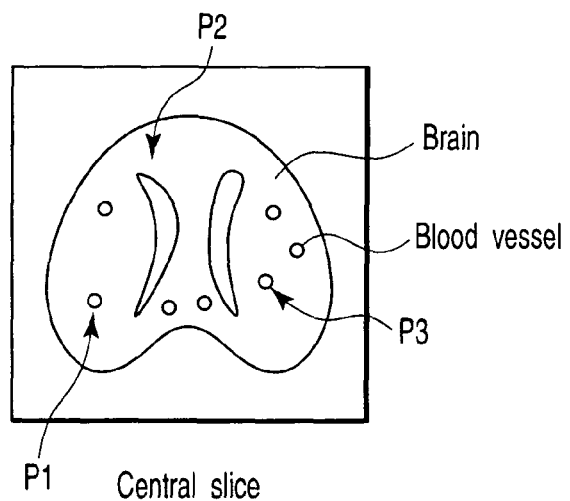
FIG. 7 is a view showing a central slice associated with a step SA1 in FIG. 5.

FIG. 7 is a view showing a mid-plane slice. Referring to FIG. 7, the round portions represents blood vessels, and P1, P2, and P3 respectively represent a pixel at the position of an artery, a pixel at a position where there is no blood vessel, and a pixel at the position of a vein.

Figure 8:
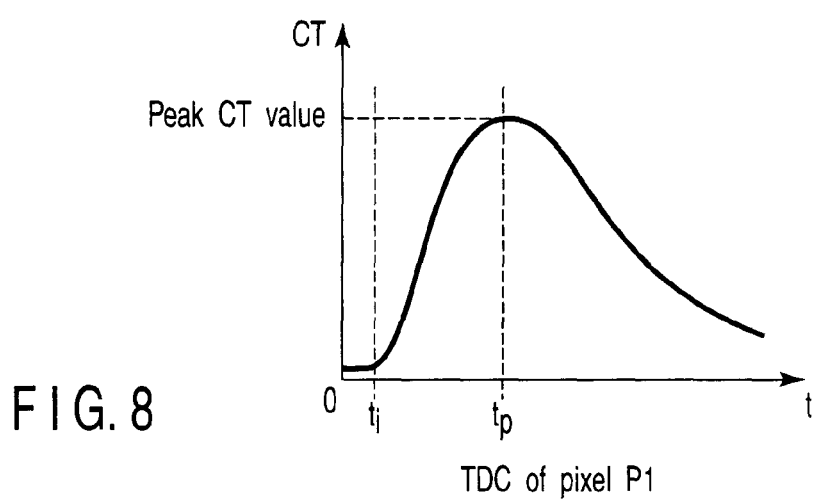
FIG. 8 is a graph showing a contrast medium time density curve (TDC) at a pixel P1 of a central slice image in FIG. 7.

FIG. 8 is a graph showing a contrast medium time density curve (TDC) at the pixel P1 at the position of the artery in FIG. 7. As shown in FIG. 8, the CT value of the pixel P1 is almost zero at a reference time (t=0), and increases at time ti when a contrast medium flows into the head portion. The CT value reaches a peak at time tp, and then decreases afterward. A characteristic of the waveform of the TDC at the position of the artery is that the CT value increases immediately after time ti when the contrast medium flows into the head portion.

Figure 9:
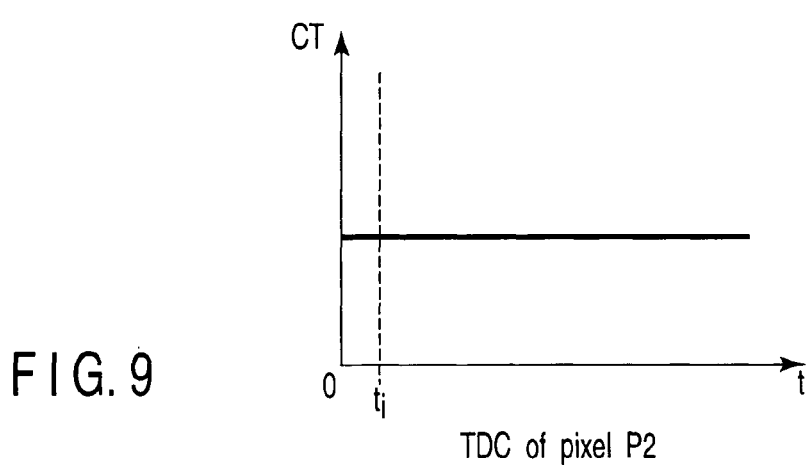
FIG. 9 is a graph showing a contrast medium time density curve (TDC) at a pixel P2 of the central slice image in FIG. 7.

FIG. 9 is a view showing a TDC at the pixel P2 at the position where there is no blood vessel in FIG. 7. As shown in FIG. 9, the CT value of the pixel P2 does not change with time and is constant. That is, a characteristic of the TDC at the position where there is no blood vessel is that the CT value does not change with time.

FIG. 10 shows a TDC at the pixel P3 at the position of the vein in FIG. 7. As shown in FIG. 10, the CT value of the pixel P3 increases some time after time ti when the contrast medium flows into the head portion, and reaches a peak value at time tq (q>p). The CT value decreases afterward. A characteristic of the TDC at the position of the vein is that the CT value increases some time after time ti when the contrast medium flows into the head portion. Although the first embodiment has exemplified the slice image at the central position, the present invention is not limited to this and can be applied to a slice image at another position.

The region-of-interest setting unit 18 identifies a TDC, of the TDCs of all the pixels generated in step SA1, which has a waveform approximate to a reference artery waveform (step SA2). The reference artery waveform is stored in the storage unit 20 in advance. This is the waveform of a TDC having a shape typical to an artery like that shown in FIG. 8. The storage unit 20 also stores a reference vein waveform which is the waveform of a TDC having a shape typical to a vein like that shown in FIG. 10. The region-of-interest setting unit 18 classifies the TDCs of all pixels into arteries, veins, and others on the basis of the reference artery waveform and the reference vein waveform, and specifies pixels estimated to correspond to the arteries.

The region-of-interest setting unit 18 then sets ROIs in a region including the identified pixels on the arteries (step SA3). FIG. 11 is a view showing ROIs set at the artery positions on the central slice image in FIG. 7. FIG. 11 shows a case wherein ROIs are set at and near the pixels on all the arteries.

The TDC generating unit 23 then generates an artery TDC unique to the subject which is associated with adding and averaging of the CT values in the set ROIs (step SA4). The TDCs of all the pixels classified in step SA3 are TDCs unique to the subject. Therefore, the TDC obtained by adding and averaging a plurality of TDCs of pixels estimated to be located at the positions of the arteries is an artery TDC unique to the subject. FIG. 12 is a graph showing an artery TDC unique to the subject which is associated with adding and averaging of the CT values in the ROIs set on the central slice in step SA3.

The TDC generating unit 23 specifies the peak CT value of the artery TDC unique to the subject (step SA5). The TDC generating unit 23 then determines an artery phase to a predetermined time width centered on scanning time tk corresponding to the peak CT value (step SA6). It is generally known that a predetermined period centered on scanning time tk corresponding to the peak CT value of an artery TDC corresponds to an artery phase, and a subsequent period corresponds to a vein phase. The predetermined time width varies depending on the scanning region, contrast medium injection position, subject, heart rate, and the like, and is empirically determined. With this operation, the artery phase/vein phase specifying routine SA is terminated.

Referring back to FIG. 2, processing following the processing procedure in the first embodiment will be described. When the artery phase/vein phase specifying routine SA is terminated, the blood vessel running volume data file (VB) generating routine SB starts. The blood vessel running volume data file VB is a volume data file from which a background (residues, internal tissue, and the like) is removed and which can specify an artery structure, vein structure, or overall blood vessel structure. Consider, for the sake of simplicity, only a case wherein an artery running volume data file is generated in the blood vessel running volume data file generating routine SA.

Figure 13:
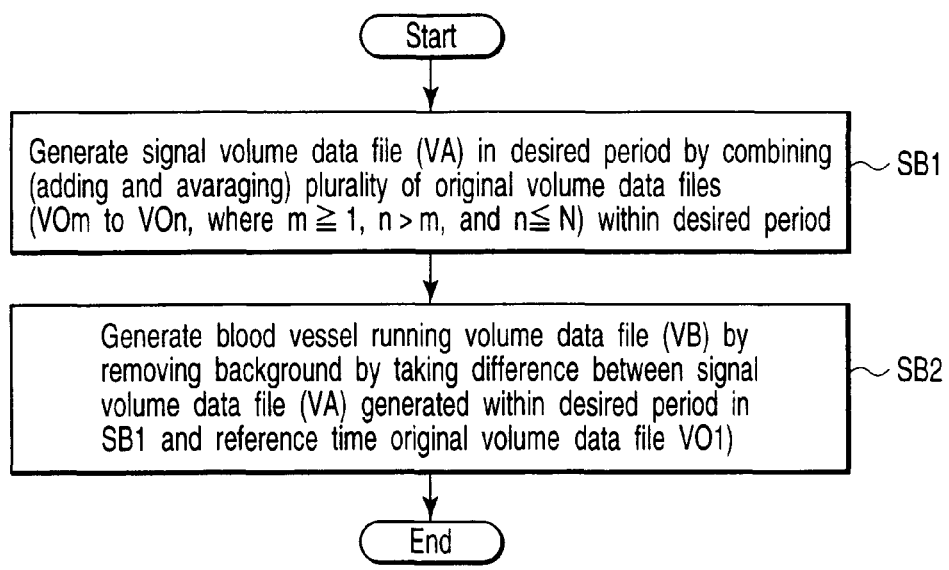
FIG. 13 is a flowchart showing a processing procedure in a volume data file (VB) generating routine obtained by extracting vessel running in FIG. 2.

A processing procedure in the volume data file (VB) generating routine SB which has extracted artery running will be described with reference to FIG. 13. First of all, as preprocessing for the generation of the artery running volume data file VB, the blood vessel structure extraction unit 13 adds and averages all original volume data files (VOm to VOn where m≧1, n>m, and n≦N) in the artery phase determined by the TDC generating unit 23 to generate the signal artery phase volume data file VA (step SB2). Adding and averaging only the original volume data files VOm to VOn in the artery phase will generate one volume data file containing only arteries without any veins.

Figure 14:
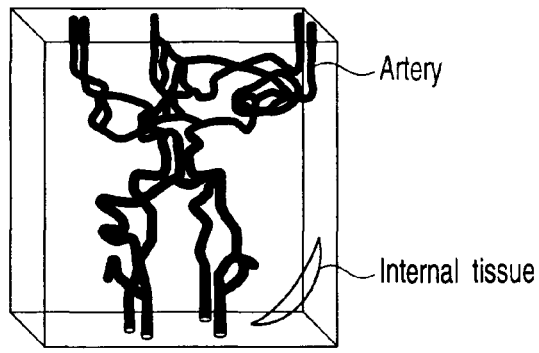
FIG. 14 is a view showing an artery phase volume data file VA generated in step SB2 in FIG. 13.

FIG. 14 is a view showing the artery phase volume data file VA. As shown in FIG. 14, adding and averaging processing makes residues randomly existing in the respective volume data files VOm to VOn less noticeable in the artery phase volume data file VA. Note, however, that actual tissue in the body exists.

In order to remove internal tissue, the blood vessel structure extraction unit 13 takes a difference between the artery phase volume data file VA and the reference time volume data file VO1 and generates the artery running volume data file VB (step SB3). The artery phase volume data file VA includes the overall arteries and internal tissue. The reference time original volume data file VO1 contains no artery but includes internal tissue.

Figure 15:
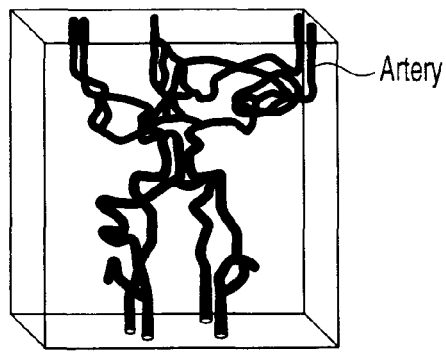
FIG. 15 is a view showing the volume data file VB obtained by extracting vessel running which is generated in step SB3 in FIG. 13.

FIG. 15 is a view showing the artery running volume data file VB generated as a result of taking a difference between the artery phase volume data file VA and the reference time original volume data file VO1. As shown in FIG. 15, the artery running volume data file VB contains neither residue nor internal tissue but includes only the arteries.

With this operation, the blood vessel running volume data file (VB) generating routine SB is terminated.

Referring back to FIG. 2, processing following the processing procedure in the first embodiment will be described. Consider, for the sake of simplicity, only a case wherein the blood vessel running volume data VB is the artery running volume data VB, and the subsequent processing is associated with only arteries.

When the artery running volume data file (VB) generating routine SB is terminated, the difference volume data generating unit 22 generates a plurality of difference volume data files (VCm to VCn−1 (m≧1, n>m, and n≦N)) by taking differences between the original volume data files, of only the original volume data files VOm to VOn in the artery phase, which correspond to adjacent scanning times (step S03). More specifically, the difference volume data generating unit 22 generates the difference volume data file VCm by taking a difference between the original volume data file VOm at given scanning time m and an original volume data file VOm+1 at the next scanning time (m+1). This operation is represented by symbols as (VOm)−(VOm+1)=VCm. The suffixes m and n used here represent the start and end times of an artery phase.

FIGS. 16(a) to 16(c) are views showing a plurality of difference volume data files. Assume that m=1<a<b<c<n. FIG. 16(a) shows a difference volume data file VC1 generated as a result of taking a difference between the reference time original volume data file VO1 and the original volume data file VOa. FIG. 16(b) shows a difference volume data file VCa generated as a result of taking a difference between the original volume data file VOa and the original volume data file VOb. FIG. 16(c) shows a difference volume data file VCb generated as a result of taking a difference between the original volume data file VOb and the original volume data file VOc. A plurality of difference volume data files generated in this step contain no internal tissue but contain residues.

The user then determines whether to remove the residues contained in the plurality of difference volume data files VCm to VCn−1 (step S04). In this case, the control unit 12 or the like may automatically determine, on the basis of the volume of the residue region contained in each of the difference volume data files VCm to VCn−1, whether the residue is removed.

A case wherein no residue is removed will be described first. If no residue is to be removed, when step S03 is complete, the blood vessel volume data generating unit 26 extracts blood vessel portions from the plurality of difference volume data files VCm to VCn−1, and generates a new volume data file by overlaying the blood vessel portions along artery running (step S05). The respective blood vessel portions can be arranged at accurate positions by overlaying the respective blood vessel portions extracted from the difference volume data files VCm to VCn−1 along artery running in the volume data file VB obtained by extracting artery running. The volume data file generated by arranging the respective blood vessel portions along artery running will be referred to as the artery volume data file VD.

Figure 17:
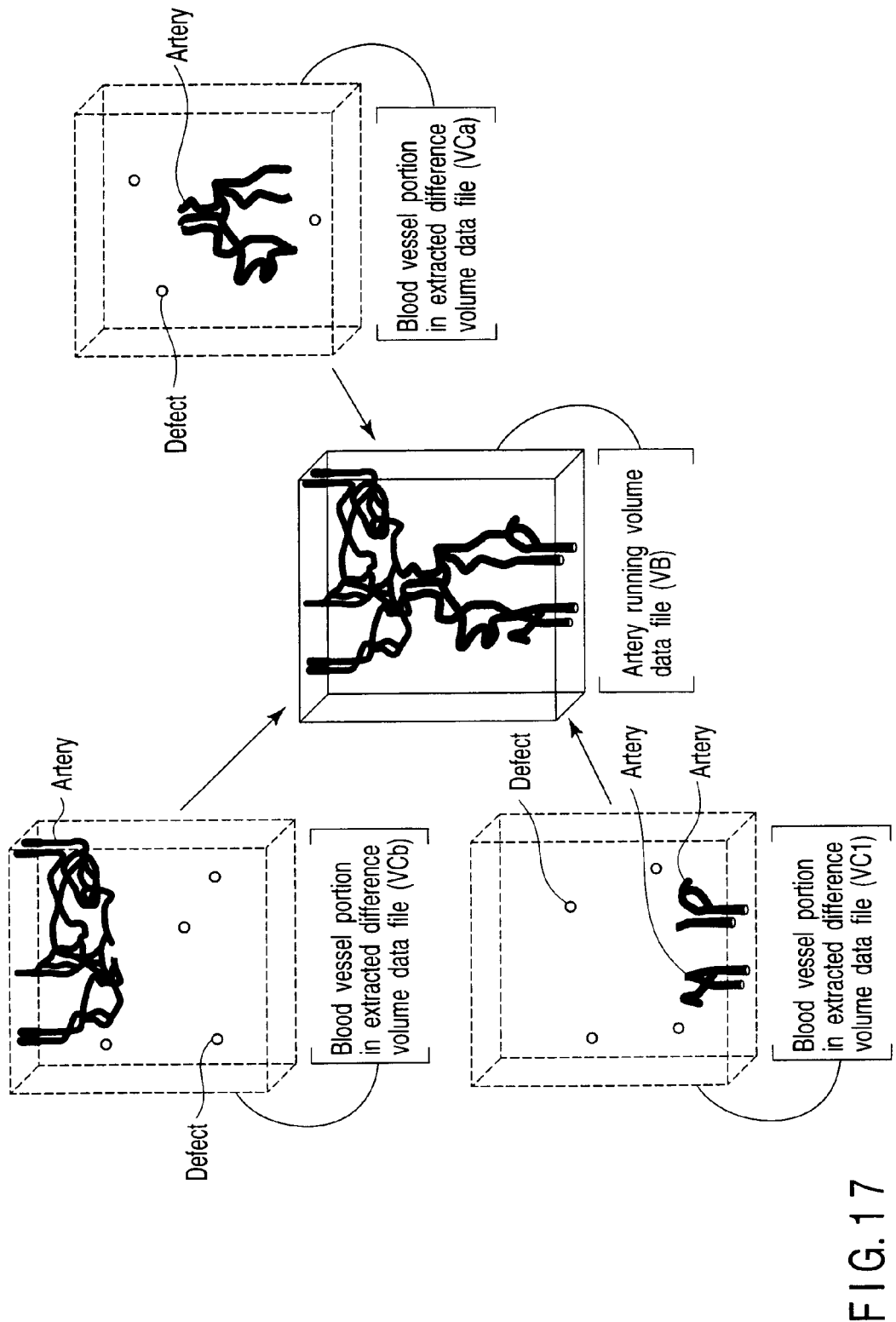
FIG. 17 is a view for explaining the processing of overlaying a plurality of blood vessel portions extracted from a plurality of difference volume data files along vessel running in step S05 in FIG. 2.

FIG. 17 is a view for explaining the processing of overlaying extracted blood vessel portions on artery running. As shown in FIG. 17, the blood vessel volume data generating unit 26 overlays the extracted difference volume data file VC1, the extracted difference volume data file VCa, and the extracted difference volume data file VCb along artery running in the artery running volume data file VB. In this overlay processing, the residues contained in the difference volume data files VCm to VCn−1 are overlaid at the same time.

Figure 18:
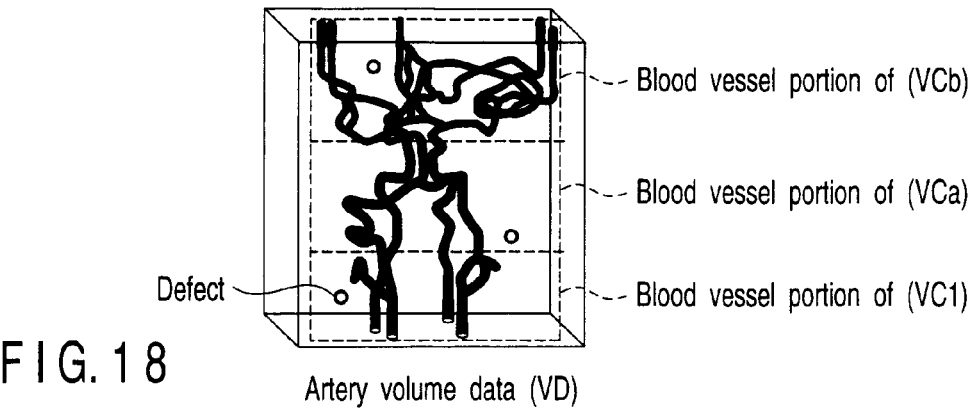
FIG. 18 is a view showing the vessel volume data file VD generated in step S05 in FIG. 2.

FIG. 18 is a view showing the vessel volume data file VD generated by overlay processing. The respective blood vessel portions are distinguishably arranged in the vessel volume data file VD.

The display image generating unit 16 generates a display image by providing color or luminance information for each blood vessel portion in the vessel volume data file VD on the basis of the scanning time, and performing MPR processing (Multi Planar Reconstruction) and rendering processing with respect to the vessel volume data file VD provided with the color or luminance information (step S06). The scanning time of this blood vessel portion is determined on the basis of the adjacent scanning times of two original volume data files on which the blood vessel portion is based. More specifically, of the adjacent scanning times, the earlier time is set as the scanning time of the blood vessel portion. Obviously, the scanning time of the blood vessel portion need not be limited to this scanning time. For example, this scanning time may be the later one of the adjacent scanning times or the intermediate time between them. The display image generating unit 16 provides, for example, color information of red or luminance information for each blood vessel portion of the vessel volume data file VD such that the color gradually increases in color density from a blood vessel portion at an earlier scanning time to a blood vessel portion at a later scanning time.

Figure 19:
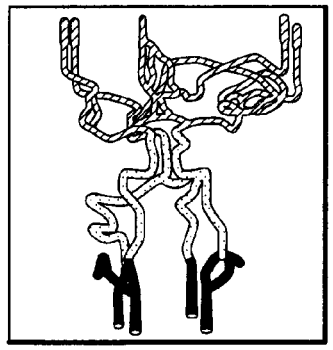
FIG. 19 is a view showing a display image provided with color or luminance information which is generated in step S06 in FIG. 2.

An image display unit 17 displays the generated display image (step S07). FIG. 19 is a view showing a display image provided with color information. As shown in FIG. 19, displaying the blood vessel portions in different colors depending on the scanning times allows the user to know how much blood has moved in the interval between adjacent scanning times.

For the sake of simplicity, the above description has exemplified only the case wherein a display image associated with arteries is generated. However, it is possible to generate a display image associated with veins or all blood vessels by replacing "artery" and "arteries" with "vein" and "veins" or "all blood vessels" in the above description. A case wherein it is determined in step S04 that residue processing is performed will be described next. When residue processing is to be performed, a residue removal routine SC, SC, or SE is started after the completion of step S03. Defect processing is performed by using the blood vessel running volume data file VB. This processing includes three kinds of processing routines SC, SD, and SE. First of all, residue processing routine 1 SC will be described first.

Defect processing routine 1 SC is a routine for enlarging the blood vessel portion in the blood vessel running volume data file VB and performing residue processing for the respective difference volume data files VCm to VCn−1 on the basis of the enlarged blood vessel portion.

Figure 20:
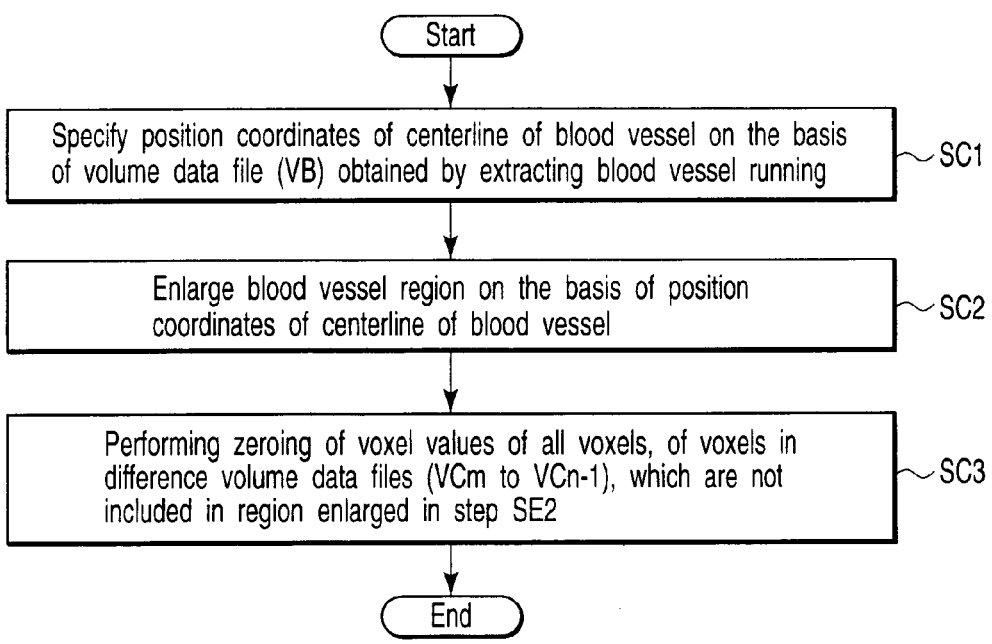
FIG. 20 is a flowchart showing a processing procedure in residue removal routine 1 in FIG. 2.

FIG. 20 is a flowchart showing a processing procedure in the residue processing routine SC. First of all, the zeroing unit 21 specifies the position of the centerline of a blood vessel on the basis of the blood vessel running volume data file VB (step SC1).

FIG. 21 is a view for explaining the processing of specifying the position coordinates of the centerline of a blood vessel. As shown in FIG. 21, the zeroing unit 21 specifies the position coordinates of the centerline of a blood vessel by tracking the blood vessel (the hatched region in FIG. 21) in the blood vessel running volume data file VB. Let r1 be the diameter of the blood vessel. Obviously, the diameter r1 changes depending on the position on the blood vessel.

The zeroing unit 21 then enlarges the blood vessel region on the basis of the position coordinates of the centerline of the blood vessel (step SC2). FIG. 22 is a view for explaining the processing of enlarging the blood vessel region in the blood vessel running volume data file VB. As shown in FIG. 22, the zeroing unit 21 enlarges the blood vessel region. This enlarged region will be referred to as an enlarged region. The centerline of the enlarged region coincides with the centerline of the blood vessel. A diameter r2 of the enlarged region is larger than the diameter r1 of the blood vessel. Note that the diameter r2 of the enlarged region may be constant or change in accordance with the diameter r1 of the artery. The diameter r2 of the enlarged region is, for example, about 8 mm if it is constant.

The zeroing unit 21 then zeroes the voxel values of regions, of all the voxels in the respective difference volume data files VCm to VCn−1, which are not included in the enlarged region (step SC3). The zeroing unit 21 specifies a region which is not included in the enlarged region in each of the difference volume data files VCm to VCn−1 on the basis of the position coordinates of the enlarged region, and zeroes the voxel value of the region which is not included in the enlarged region. The region which is not included in the enlarged region is a region other than a blood vessel. That is, this region is a residue. Therefore, residue processing is performed by zeroing the voxel value of the region which is not included in the enlarged region. When step SC3 is performed, residue processing routine 1 SC is terminated.

A processing procedure in residue processing routine 2 SD will be described next with reference to FIG. 23. Defect processing routine 2 is a routine for performing residue processing on the basis of the volume of the blood vessel portion and the volume of the residue.

First of all, the zeroing unit 21 extracts regions as blood vessel candidates by performing threshold processing with respect to the respective difference volume data files VCm to VCn−1 (step SD1). The blood flow calculating unit 15 calculates the volume of each of all the regions as blood vessel candidates included in the respective difference volume data files VCm to VCn−1 (step SD2).

The zeroing unit 21 then specifies a region, of all the regions as blood vessel candidates, which does not satisfy a predetermined volume (step SD3), and zeroes the voxel value of the region which does not satisfy the predetermined volume (step SD4). The region of each blood vessel portion should have a predetermined volume or more instead of a small volume of about one or two voxels in order to have continuity. That is, a region having a volume equal to or more than the predetermined volume is a blood vessel region, and a region having a volume equal to or less than the predetermined volume is a residue region. The zeroing unit 21 zeroes the voxel value of each region having a volume equal to or smaller than a predetermined volume. A predetermined volume is determined on the basis of the blood vessel volume data file VD, difference volume data files VCm to VCn−1, or experiences. When step SD3 is performed, residue processing routine 2 is terminated.

Figure 24:
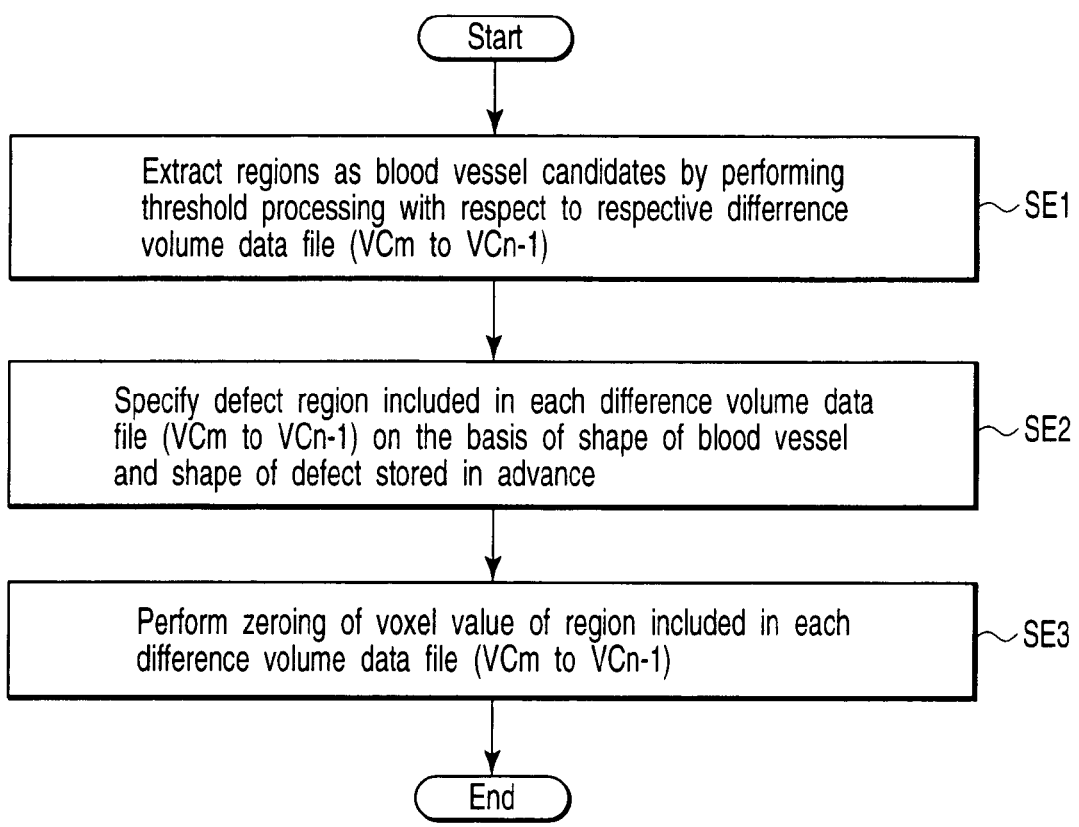
FIG. 24 is a flowchart showing a processing procedure in residue removal routine 3 in FIG. 2.

A processing procedure in residue processing routine 3 SE will be described with reference to FIG. 24. Defect processing routine 3 is a routine for performing residue processing on the basis of the shape of a blood vessel portion and the shape of a residue.

First of all, the zeroing unit 21 extracts regions as blood vessel candidates by performing threshold processing with respect to the respective difference volume data files VCm to VCn−1 (step SE1). The zeroing unit 21 specifies a residue region included in each of the difference volume data files VCm to VCn−1 on the basis of the shape of a blood vessel and the shape of a residue stored in the storage unit 20 (step SD2). The region of a blood vessel portion has a shape with linearity. Therefore, a region having a shape other than the shape with linearity, e.g., a point-like shape, is a residue region. Blood vessel shape and residue shape candidates are determined in advance on the basis of the artery volume data file VD, the difference volume data files VCm to VCn−1, or experiences, and are stored in the storage unit 20 in advance.

The zeroing unit 21 then zeroes the voxel value of each region which does not have the shape of a blood vessel or has the shape of a residue (step SD3). When step SD3 is performed, residue processing routine 3 is terminated.

It suffices to perform residue processing with respect to the plurality of difference volume data files VCm to VCn−1 by using one of the above three kinds of residue processing routines SC, SD, and SE or by combining a plurality of routines of the three types of residue processing routines SC, SD, and SE. It depends on the user.

According to the first embodiment, therefore, it is possible to grasp a blood flow state in multi-slice CT.

Second Embodiment

Figure 25:
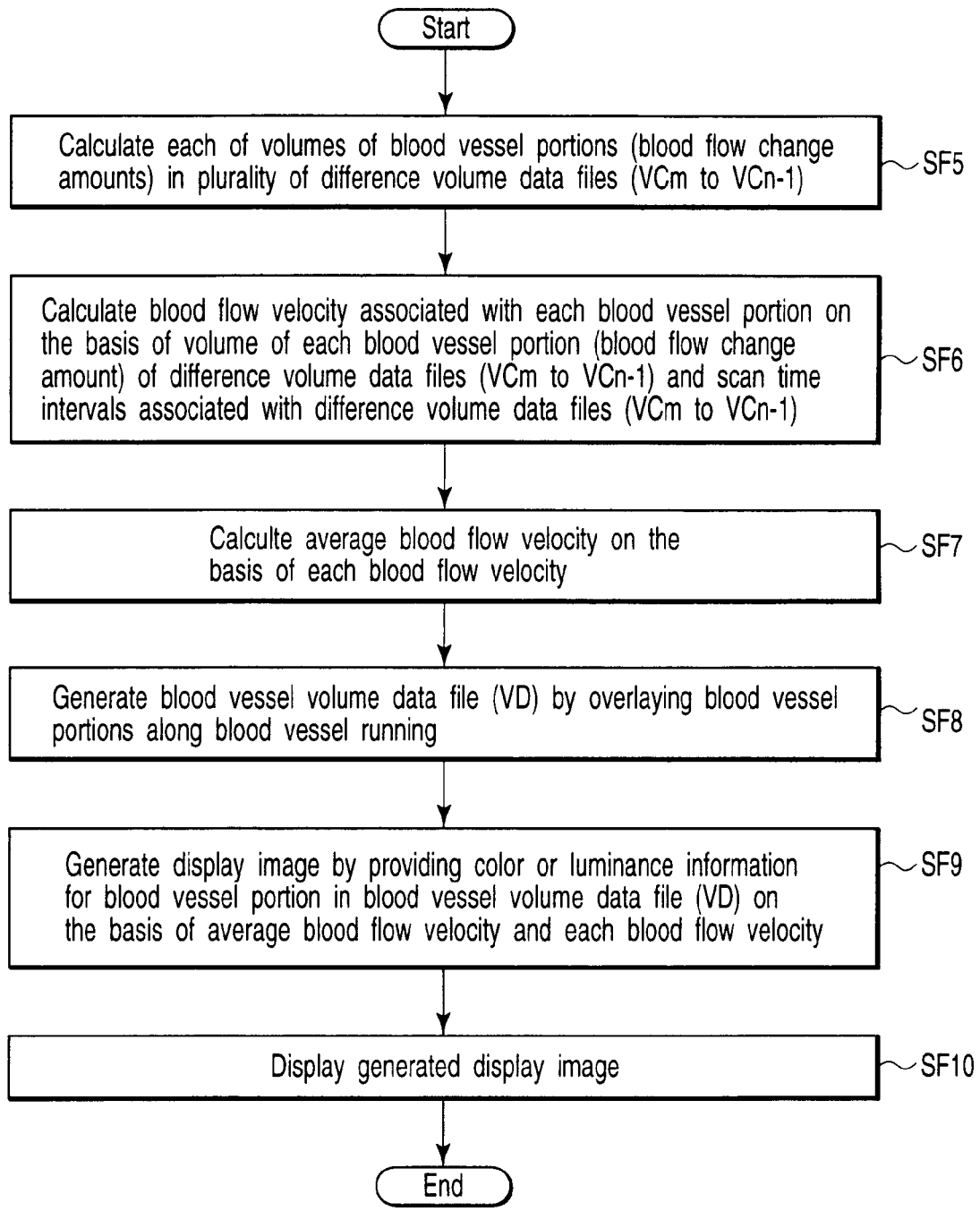
FIG. 25 is a flowchart showing a processing procedure in the second embodiment of the present invention.

The first embodiment has exemplified the case wherein the display image generating unit 16 provides color information for a blood vessel portion on the basis of the scanning time of the blood vessel portion which is extracted from each of difference volume data files VCm to VCn−1 by the display image generating unit 16. The second and third embodiments will exemplify coloring methods different from that of the first embodiment. A processing procedure in the second embodiment will be described below with reference to FIG. 25. Since the constituent elements of the second embodiment are the same as those of the first embodiment, they are denoted by the same reference numerals, and a description will not be repeated. Since the processing in steps SF1 to SF4 is the same as that in steps S01 to S04, a description thereof will not be repeated.

After residue removable is determined, a blood flow calculating unit 15 calculates the volumes of blood vessel portions in the plurality of difference volume data files VCm to VCn−1 (step SF5). The calculated volume of each blood vessel portion is the same as that of a contrast medium flowing into a blood vessel in a scan time interval. The volume of a blood vessel portion can therefore be regarded as a blood flow change amount.

The blood flow calculating unit 15 calculates a blood flow velocity associated with the volume of each blood vessel portion (blood flow change amount) on the basis of the volumes of blood vessel portions (blood flow change amounts) in the difference volume data files VCm to VCn−1 and scan time intervals associated with the difference volume data files VCm to VCn−1 (step SF6). The blood flow calculating unit 15 obtains an average blood flow velocity on the basis of each blood flow velocity (step SF7). A blood vessel volume data generating unit 26 then generates an artery volume data file VD by extracting blood vessel portions from the difference volume data files VCm to VCn−1 and overlaying the blood vessel portions along artery running (step SF8).

A display image generating unit 16 then generates a display image by providing color or luminance information for each blood vessel portion in the artery volume data file VD on the basis of an average blood flow velocity and each blood flow velocity, and performing MPR processing (Multi Planar Reconstruction) and rendering processing with respect to the artery volume data file VD provided with the color or luminance information (step SF9). For example, the blood flow velocity in a given blood vessel portion is compared with the average blood flow velocity. If the blood flow velocity in the given blood vessel portion is lower than the average blood flow velocity, color information of blue is provided for the blood vessel portion. If the blood flow velocity in the given blood vessel portion is higher than the average blood flow velocity, color information of red is provided for the blood vessel portion. In addition, the color density of information to be provided for a given blood vessel portion is changed in accordance with the magnitude of the difference between a blood flow velocity in the blood vessel portion and the average blood flow velocity. For example, color information with lower color density is provided for a blood vessel portion as the magnitude of the difference decreases, and vice versa.

An image display unit 17 displays the generated display image (step SF10). The display image displayed here has blood vessel portions colored differently depending on the blood flow velocities. This allows to grasp the blood flow velocity states of the respective blood vessel regions.

For the sake of simplicity, the description of the second embodiment has exemplified only the case wherein a display image associated with arteries is generated. However, it is possible to generate a display image associated with veins or all blood vessels by replacing "artery" and "arteries" with "vein" and "veins" or "all blood vessels" in the above description.

According to the second embodiment, therefore, it is possible to grasp blood flow states in multi-slice CT.

Third Embodiment

Figure 26:
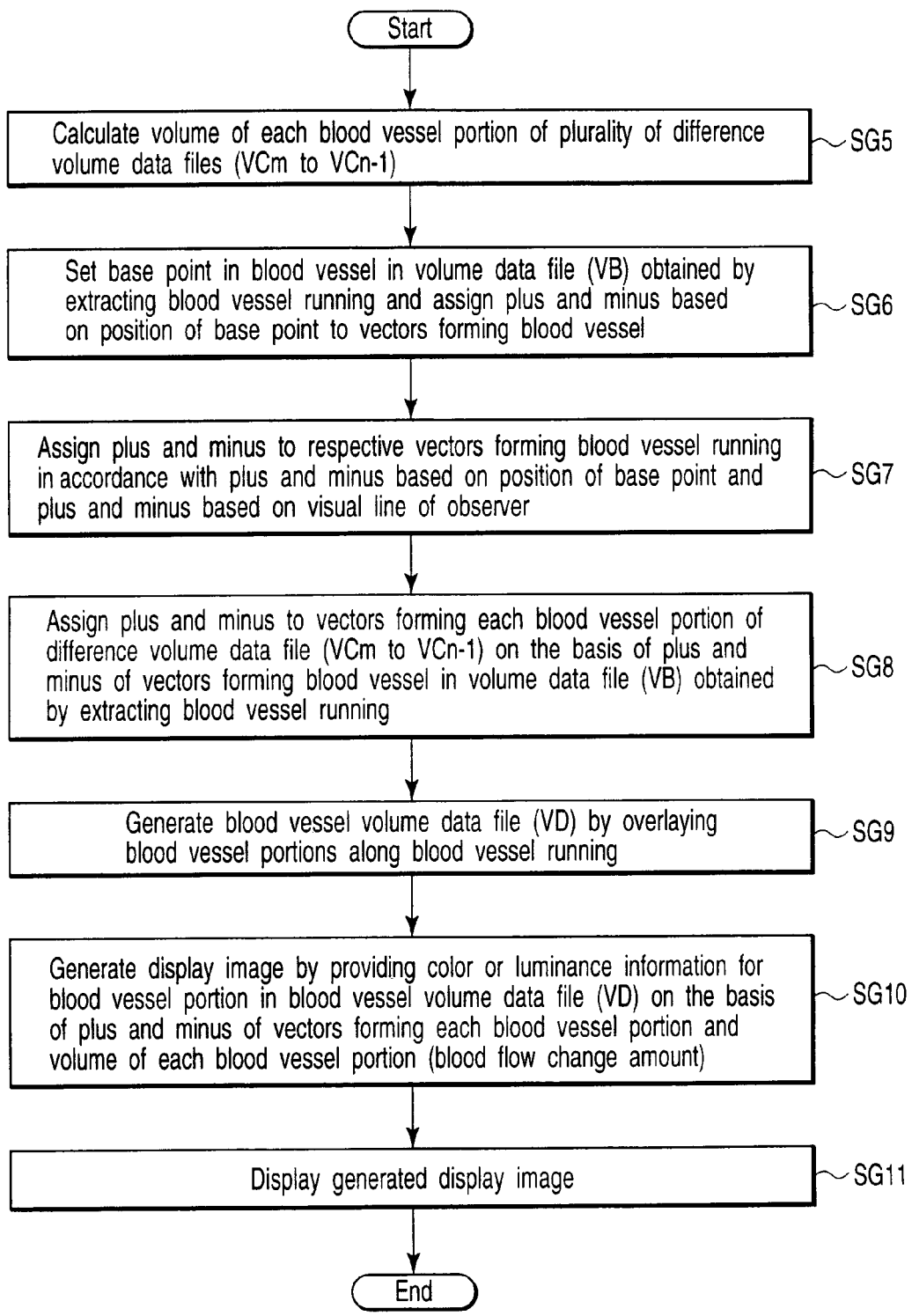
FIG. 26 is a flowchart showing a processing procedure in the third embodiment of the present invention.

A processing procedure in the third embodiment will be described below with reference to FIG. 26. Since the constituent elements of the third embodiment are the same as those of the first and second embodiments, they are denoted by the same reference numerals, and a description thereof will not be repeated. Since the processing in steps SG1 to SG4 is the same as that in steps S01 to S04, a description thereof will not be repeated.

After residue removable is determined, a blood flow calculating unit 15 calculates the volumes of blood vessel portions in a plurality of difference volume data files VCm to VCn−1 (step SG5).

Figure 27:
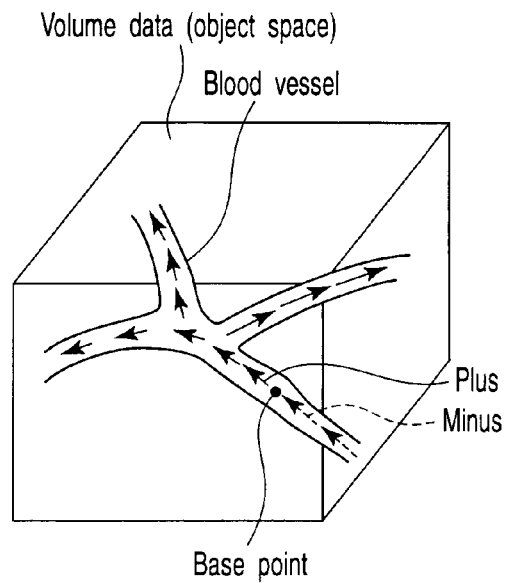
FIG. 27 is a view for explaining the processing of setting a base point in a blood vessel and assigning plus and minus based on the base point to vectors which form blood vessels.

The blood flow calculating unit 15 sets a base point in an artery in an artery running volume data file VB and assigns plus and minus based on the base point to a plurality of vectors which form arteries (step SG6). FIG. 27 is a view for explaining processing in step SG6. As shown in FIG. 27, first of all, the blood flow calculating unit 15 sets a base point at an arbitrary position in an artery in the artery running volume data file VB. When the base point is set, the blood flow calculating unit 15 assigns plus and minus to vectors (solid and broken line arrows in FIG. 27) which form arteries. More specifically, the blood flow calculating unit 15 assigns plus (the solid line arrows in FIG. 27) to vectors on one side of the base point set in the artery, and assigns minus (the broken line arrows in FIG. 27) to vectors on the other side.

Figure 28:
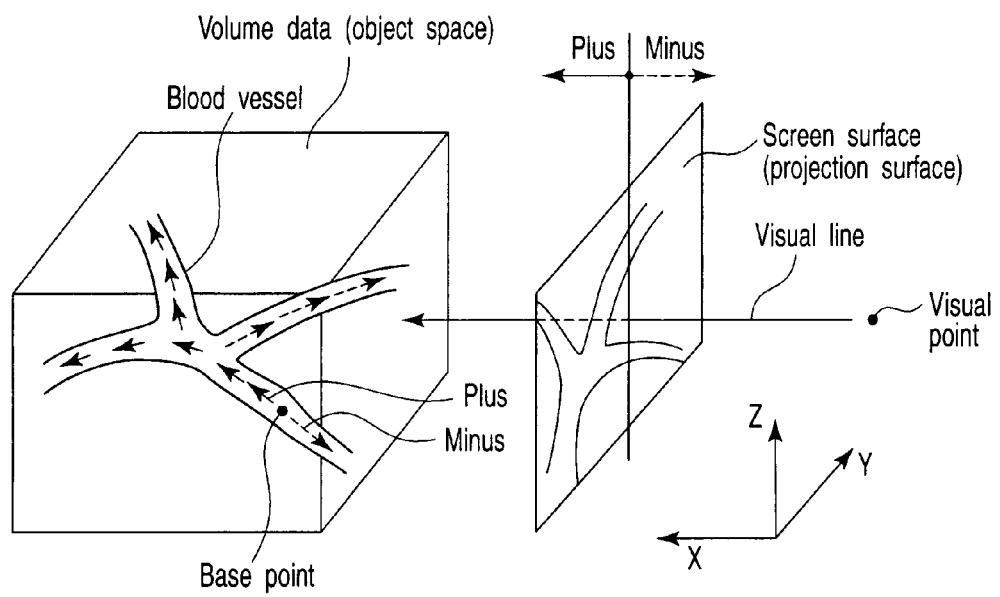
FIG. 28 is a view for explaining the processing of assigning plus and minus to vectors which form blood vessels in step SG7 in FIG. 26.

The blood flow calculating unit 15 respectively assigns plus and minus to a plurality vectors forming blood vessel running on the basis of plus and minus based on the base point and plus and minus based on the visual line (step SG7). FIG. 28 is a view for explaining processing in step SG7. As shown in FIG. 28, the screen surface (projection surface) is defined as a Z-Y plane, and the visual line extending from the visual point and intersecting the screen surface at a right angle is defined as the X-axis. Assume that the same direction as that of the visual line (the +X direction in FIG. 28) is defined as minus based on the visual line, and the reverse direction to the visual line (the −X direction in FIG. 28) is defined as minus based on the visual line. Assume that the vectors forming the arteries in the volume data file (object space) are seen through the screen surface. In this case, when one of the vectors forming the arteries, whose sign based on the base point is "plus", moves to the back side of the screen surface (in the +X direction in FIG. 28; "plus" based on the visual line), since "plus" based on the base point coincides with "plus" based on the visual line, this vector is regarded as "plus" (a solid line arrow in a solid line blood vessel portion in FIG. 28). Likewise, when one of the vectors forming the arteries, whose sign based on the base point is "plus", moves to the front side of the screen surface (in the −X direction in FIG. 28; "minus" based on the visual line), since "minus" based on the base point does not coincide with the "minus" sign based on the visual line, this vector is regarded as "minus" (a broken line arrow in a solid line blood vessel portion in FIG. 28). The direction of each blood flow is determined in this manner. Assume that when the sign of one of the vectors forming the arteries which is based on the base point is "minus", the vector is regarded as a "minus" vector (a broken line arrow in a solid line blood vessel portion in FIG. 28).

The blood flow calculating unit 15 assigns plus and minus to vectors forming the respective blood vessel portions in the difference volume data files VCm to VCn−1 on the basis of the signs of the vectors forming the arteries in the volume data file VB obtained by extracting artery running (step SG8). A blood vessel volume data generating unit 26 then generates an artery volume data file VD by extracting blood vessel portions from the plurality of the difference volume data files VCm to VCn−1 and overlaying them along artery running (step SG9).

A display image generating unit 16 then generates a display image by providing color or luminance information for each blood vessel portion in the artery volume data file VD on the basis of the signs of the vectors forming the respective blood vessel portions and the volumes of the respective blood vessel portions (blood flow change amounts), and performing MPR processing (Multi Planar Reconstruction) and rendering processing with respect to the artery volume data file VD provided with the color or luminance information (step SG10). For example, the display image generating unit 16 provides color information of red for a blood vessel portion if the direction of the vector of the blood vessel portion is minus, and provides color information of blue for a blood vessel portion if the direction of the vector is minus. The display image generating unit 16 further provides a blood vessel portion with color information whose color density changes in accordance with the magnitude of the volume of the blood vessel portion (blood flow change amount). For example, color information with lower color density is provided for a blood vessel portion as the magnitude of the volume of the blood vessel portion (blood flow change amount) decreases, and vice versa.

An image display unit 17 then displays the generated display image (step SG11). The display image displayed here has blood vessel portions colored differently depending on the volumes of the blood vessel portions (blood flow change amounts) and the directions of blood flows. This allows to grasp the volumes of the respective blood vessel portions (blood flow change amounts) and the directions of the blood flows.

For the sake of simplicity, the above description has exemplified only the case wherein a display image associated with arteries is generated. However, it is possible to generate a display image associated with veins or all blood vessels by replacing "artery" and "arteries" with "vein" and "veins" or "all blood vessels" in the above description.

According to the third embodiment, therefore, it is possible to grasp blood flow states in multi-slice CT.

Fourth Embodiment

The fourth embodiment will be described next. This embodiment is configured to generate volume data containing arteries and veins and calculate and display parameters associated with blood flows with respect to all the blood vessels by using the volume data. That is, a medical image processing apparatus or X-ray computed tomographic apparatus according to this embodiment generates volume data containing artery and vein phases after step SA in FIG. 2 and performs processing in step SB and the subsequent steps by using the volume data. This arrangement can acquire parameters associated with blood flows with respect to all the blood vessels included in a scanning region. Note that when parameters associated with blood flows are to be displayed in step S07, it is preferable to display them in a form that allows to visually discriminate arteries from veins, for example, displaying parameters associated with arteries in red, and those associated with veins in blue.

Note that the present invention is not limited to the above embodiments, and constituent elements can be variously modified and embodied at the execution stage within the spirit and scope of the invention. The following are concrete modifications.

(1) As a medical image processing apparatus for performing medical image processing characteristic to this embodiment, there is provided a first medical image processing apparatus 80 comprising a storage unit 20 which stores a plurality of original volume data files, a difference volume data generating unit 22 which generates a plurality of difference volume data files corresponding to different scanning times by obtaining differences between the original volume data files, and a display image generating unit 16 which generates a display image provided with color or luminance information corresponding to the respective scanning times on the basis of the plurality of difference volume data (FIG. 1).

(2) As a medical image processing apparatus for performing medical image processing characteristic to this embodiment, there is provided a second medical image processing apparatus 90 comprising a storage unit 20 which stores a plurality of original volume data files, a difference volume data generating unit 22 which generates a plurality of difference volume data files corresponding to different scanning times by obtaining differences between the original volume data files, a blood flow calculating unit 15 which obtains blood flow velocity information on the basis of difference volume data, and a display image generating unit 16 which generates a display image provided with color or luminance information corresponding to the blood flow velocity information on the basis of the plurality of difference volume data (FIG. 1).

Note that the present invention is not limited to the above embodiments, and constituent elements can be variously modified and embodied at the execution stage within the spirit and scope of the invention. Various inventions can be formed by proper combinations of a plurality of constituent elements disclosed in the above embodiments. For example, several constituent elements may be omitted from the all the constituent elements in each embodiment. In addition, constituent elements of the different embodiments may be combined as needed.

What is claimed is:

1. An X-ray computed tomographic apparatus comprising:
an X-ray tube which generates X-rays;
an X-ray detector which detects X-rays transmitted through a subject to be examined and generates projection data;
a reconstruction unit which generates a plurality of original volume data at different scanning times on the basis of the projection data;
a position-matching unit which performs positioning between said plurality of original volume data;
a difference volume data generating unit which obtains a plurality of difference volume data by performing difference processing between the original volume data at the different scanning times by using said plurality of original volume data after the positioning; and
a display image generating unit which generates a display image provided with color or luminance information corresponding to at least one of an arrival time of a contrast medium, a difference volume, a temporal change amount of difference volume, and blood flow velocity information on the basis of the plurality of difference volume data,
which further comprises a blood vessel image extraction unit which extracts a blood vessel image from the original volume data, of said plurality of original volume data after the positioning, which are obtained after and before injection of the contrast medium, and in which
the display image generating unit generates the display image by providing the blood vessel image with color or luminance information corresponding to at least one of an arrival time of a contrast medium which is obtained on the basis of said difference volume data, a difference volume, a temporal change amount of difference volume, and blood flow velocity information.

2. An apparatus according to claim 1, wherein the blood vessel image extraction unit extracts a blood vessel image on the basis of differences between said plurality of original volume data after injection of the contrast medium and the original volume data before injection of the contrast medium.

3. An apparatus according to claim 1, wherein the blood vessel image extraction unit combines said plurality of original volume data after injection of the contrast medium and extracts a blood vessel image on the basis of a difference between the combined original volume data and the original volume data before injection of the contrast medium.

4. An apparatus according to claim 1, wherein the blood vessel image extraction unit obtains the blood vessel image by extracting one of an artery and a vein.

5. An apparatus according to claim 1, wherein the blood vessel image extraction unit obtains the blood vessel image by combining a plurality of original volume data corresponding an artery phase or a vein phase.

6. An apparatus according to claim 5, wherein the blood vessel image extraction unit obtains a period corresponding to the artery phase or the vein phase on the basis of a change in density of the contrast medium.

7. An apparatus according to claim 1, wherein the blood vessel image extraction unit obtains the blood vessel image by combining a plurality of original volume data corresponding to an artery phase and a plurality of original volume data corresponding to a vein phase.

8. An apparatus according to claim 7, wherein the blood vessel image extraction unit obtains a period corresponding to the artery phase or the vein phase on the basis of a change in density of the contrast medium.

9. An apparatus according to claim 1, wherein the difference volume data generating unit obtains the plurality of difference volume data by performing difference processing between the original volume data corresponding to the adjacent scanning times.

10. An apparatus according to claim 1, further comprising a period determination unit which obtains a contrast medium density change curve on the basis of information of at least a partial region of the original volume data and determines a period of the original volume data to be combined on the basis of information of the density change.

11. A medical image processing apparatus which acquires volume data having three-dimensional information in a subject to be examined, the apparatus comprising:
   an X-ray tube which generates X-rays;
   a storage unit which stores a plurality of original volume data at different scanning times which are acquired by injecting a contrast medium into the subject;
   a position-matching unit which performs positioning between said plurality of original volume data;
   a difference volume data generating unit which obtains a plurality of difference volume data by performing difference processing between the original volume data at the different scanning times by using said plurality of original volume data after the positioning; and
   a display image generating unit which generates a display image provided with color or luminance information corresponding to at least one of an arrival time of a contrast medium, a difference volume, a temporal change amount of difference volume, and blood flow velocity information on the basis of the plurality of difference volume data,
   which further comprises a blood vessel image extraction unit which extracts a blood vessel image from the original volume data, of said plurality of original volume data after the positioning, which are obtained after and before injection of the contrast medium, and in which
   the display image generating unit generates the display image by providing the blood vessel image with color or luminance information corresponding to at least one of an arrival time of a contrast medium which is obtained on the basis of said difference volume data, a difference volume, a temporal change amount of difference volume, and blood flow velocity information.

12. An apparatus according to claim 11, wherein the blood vessel image extraction unit extracts a blood vessel image on the basis of differences between said plurality of original volume data after injection of the contrast medium and the original volume data before injection of the contrast medium.

13. An apparatus according to claim 11, wherein the blood vessel image extraction unit combines said plurality of original volume data after injection of the contrast medium and extracts a blood vessel image on the basis of a difference between the combined original volume data and the original volume data before injection of the contrast medium.

14. An apparatus according to claim 11, wherein the blood vessel image extraction unit obtains the blood vessel image by extracting one of an artery and a vein.

15. An apparatus according to claim 11, wherein the blood vessel image extraction unit obtains the blood vessel image by combining a plurality of original volume data corresponding an artery phase or a vein phase.

16. An apparatus according to claim 15, wherein the blood vessel image extraction unit obtains a period corresponding to the artery phase or the vein phase on the basis of a change in density of the contrast medium.

17. An apparatus according to claim 11, wherein the blood vessel image extraction unit obtains the blood vessel image by combining a plurality of original volume data corresponding to an artery phase and a plurality of original volume data corresponding to a vein phase.

18. An apparatus according to claim 17, wherein the blood vessel image extraction unit obtains a period corresponding to the artery phase or the vein phase on the basis of a change in density of the contrast medium.

19. An apparatus according to claim 11, wherein the difference volume data generating unit obtains the plurality of difference volume data by performing difference processing between the original volume data corresponding to the adjacent scanning times.

20. An apparatus according to claim 11, further comprising a period determination unit obtains a contrast medium density change curve on the basis of information of at least a partial region of the original volume data and determines a period of the original volume data to be combined on the basis of information of the density change.

* * * * *